United States Patent
Kuchroo et al.

(10) Patent No.: US 6,207,156 B1
(45) Date of Patent: Mar. 27, 2001

(54) SPECIFIC ANTIBODIES AND ANTIBODY FRAGMENTS

(75) Inventors: Vijay K. Kuchroo, Newton; Edward A. Greenfield, Stoughton, both of MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/040,953

(22) Filed: Mar. 18, 1998

Related U.S. Application Data

(60) Provisional application No. 60/041,038, filed on Mar. 21, 1997.

(51) Int. Cl.[7] .............. A61K 39/395; C07K 16/28; C12N 5/12

(52) U.S. Cl. .............. 424/154.1; 424/130.1; 424/133.1; 424/135.1; 424/141.1; 424/143.1; 424/144.1; 424/153.1; 424/173.1; 435/326; 435/332; 435/334; 435/343; 435/343.1; 435/343.2; 435/346; 530/387.1; 530/387.3; 530/388.1; 530/388.2; 530/388.22; 530/388.7; 530/388.73; 530/388.75

(58) Field of Search ............... 424/130.1, 133.1, 424/143.1, 154.1; 435/326, 343, 346; 530/387.1, 388.2, 388.73, 387.3, 388.22, 388.75

(56) References Cited

U.S. PATENT DOCUMENTS

| | | | |
|---|---|---|---|
| 5,085,985 | 2/1992 | Maino et al. | 435/7.24 |
| 5,242,687 | 9/1993 | Tykocinski et al. | 424/93 |
| 5,434,131 | 7/1995 | Linslev et al. | 514/2 |
| 5,449,610 | 9/1995 | Lillehoj | 435/7.24 |
| 5,455,165 | 10/1995 | Capon et al. | 435/64.7 |
| 5,474,771 | 12/1995 | Lederman et al. | 424/133.1 |
| 5,565,335 | 10/1996 | Capon et al. | 435/64.7 |
| 5,597,710 | 1/1997 | Dalie et al. | 435/69.6 |
| 5,811,097 | * 9/1998 | Allison et al. | |

FOREIGN PATENT DOCUMENTS

| | | |
|---|---|---|
| WO 95/06738 | 9/1995 | (WO) . |
| WO95/06738 | 9/1995 | (WO) . |
| WO95/33770 | 12/1995 | (WO) . |
| WO96/31229 | 10/1996 | (WO) . |

OTHER PUBLICATIONS

Ngo et al. In The Protein Folding Problem and Tertiary Structure Prediction, Merz et al. (ED) Birkhauser Boston 1994, pp. 491–495.*
Kahan et al. Curr. Opin. Immunol. 4:553–560 (1992).*
Blazar et al. J. Immunol. 157:3250–3259 (1996).*
Chung et al. J. Korean Soc. Microbiol. 28:229–237 (1993).*
Guerette, et al., "Immunosuppression with monoclonal . . . ", Transplantation, 1996, 62:7:962–967.
Judge, et al., "The In Vivo Mechanism . . . ", J. of Immunology, 1996, 2294–2299.
Sperling, et al., "CD28/B7 Interactions . . . ", J. of Immunology, 1996, 3909–3917.
Krummel, et al., "CTLA–4 Engagement . . . ", J. Exp. Med., 1996, 183:2533–2540.
Walunas, et al., "CTLA–4 Ligation Blocks . . . ", J. Exp. Med., 1996, 183:2541–2550.
Greene, et al., "Covalent Dimerization . . . ", J. Biolog. Chem., 1996, 271:43:26762–26771.
Krummel, et al., "Superantigen responses . . . ", International Immunology, 1996, 8:4:519–52.
Galea–Lauri, et al., "Novel costimulators . . . ", Cancer Gene Therapy, 1996, 3:3:202–213.
Krummel, et al., "CTLA–4 Engagement . . . ", J. Exp. Med., 1996, 183:2533–2540.
Höllsberg, et al., "Expression of a Hypoglycosylated . . . ", J. of Immunology, 1997, 4799–4805.
Kuchroo, et al., "B7–1 and B7–2 Costimulatory . . . ", Cell, 1995, 80:707–718.
Greenfield, et al., "B7.2 Expressed by . . . ", J. of Immunology, 1997, 2025–2034.
Leach, et al., "Enhancement of Antitumor . . . ", Science, 1996, 271:1734–1736.

* cited by examiner

Primary Examiner—Phillip Gambel
(74) Attorney, Agent, or Firm—Wolf, Greenfield & Sacks, P.C.

(57) ABSTRACT

The present invention relates to methods and products for immunotherapy resulting in the stimulation of T-cell proliferation. The products of the invention are peptides that bind to CTLA-4 and co-stimulate the proliferation of T-cells by inhibiting the binding of B7 to CTLA-4. Pharmaceutical compositions including such peptides are also provided. The invention further provides in vitro and in vivo therapeutic methods employing the peptides of the invention.

24 Claims, No Drawings

SPECIFIC ANTIBODIES AND ANTIBODY FRAGMENTS

This application claims priority to the U.S. Provisional Application No. 60/041,038, filed Mar. 21, 1997, entitled IMMUNOTHERAPEUTIC CTLA-4 BINDING PEPTIDES.

FIELD OF THE INVENTION

This invention relates generally to the field of immunology and specifically to peptides which bind to CTLA-4 and stimulate T-cell proliferation.

BACKGROUND OF THE INVENTION

The complex process of T-cell activation and proliferation is based on diverse interactions such as antigen presentation, cell-cell contact and soluble immune mediators e.g., cytokines or lymphokines. Many of these interactions are mediated in T-cells through surface receptors. T helper cells, for example, require for activation both the presentation of an antigen by an antigen presenting cell (APC) in association with major histocompatibility complex (MHC) and a secondary signal. The secondary signal may be a soluble factor or may involve an interaction with another set of receptors on the surface of T-cells. Antigen presentation in the absence of the secondary signal, however, is not sufficient to activate T helper cells.

The CTLA-4/CD28/B7 system is a group of proteins involved in regulating T-cell proliferation through this secondary signaling pathway. The T-cell proliferative response is controlled by the interaction of the B7 family of proteins, which are expressed on the surface of APCs, with CTLA-4 (cytotoxic T lymphocyte antigen #4) and CD28.

The B7 family of proteins is composed of structurally related glycoproteins including B7-1, B7-2, and B7-3 (Galea-Lauri et al., *Cancer Gene Therapy*, v. 3, p. 202–213 (1996); Boussiotis, et al., *Proc. Nat. Acad. Sci. USA*, v. 90, p.11059–11063 (1993)). The different B7 proteins appear to have different expression patterns on the surface of antigen presenting cells. For example B7-2 is constitutively expressed on the surface of monocytes, whereas B7-1 is not, although B7-1 expression is induced in these cells when the cells are stimulated with interferon gamma (IFN-$\gamma$). The different expression patterns may indicate a different role for each of the B7 family members. The B7 proteins is believed to be involved in the events relating to stimulation of an immune response by its ability to interact with various immune cell surface receptors. It is believed, for example, that B7 plays a role in augmenting T-cell proliferation and cytokine production through its interaction with the CD28 receptor.

CD28, a homodimeric glycoprotein having two disulfide linked 44-kd subunits, is found on 95% of CD4$^+$ and 50% of CD8$^+$ cells. Studies using monoclonal antibodies reactive with CD28 have demonstrated that CD28 is involved in a secondary signal pathway in the activation of T-cell proliferation. Antibodies which block the interaction of CD28 with its ligand have been found to inhibit T-cell proliferation in vitro resulting in antigen specific T cell energy. (Harding et al., *Nature*, v. 356, p. 607 (1991)).

Recently a T-cell surface receptor protein, CTLA-4, having approximately 20% sequence homology to CD28 was identified. Although CTLA-4 is not endogenously expressed on T-cell surfaces, its expression is induced when CD28 interacts with B7 on the surface of an APC. Once CTLA-4 is expressed on the surface of the T-cell it is capable of interacting with B7.

Several groups have hypothesized that CTLA-4 and CD28 might have opposing effects on a T-cell and that CTLA-4 and CD28 might compete for binding of B7. (Krummel et al., *International Immunology*, v. 8, p.519–523 (1995); Galea-Lauri et al., *Cancer Gene Therapy*, v. 3, p. 202–213 (1996)). When a T-cell is presented an antigen by APC and B7 interacts with CD28 on the T-cell surface, a secondary signal is created which stimulates the T-cell to proliferate. When, however, B7 interacts with CTLA-4 the secondary signal is not created. It is still unclear whether the interaction of CTLA-4 with B7 initiates an inhibitory signaling pathway to prevent the cell from proliferating or whether the interaction of CTLA-4 with B7 simply acts to reduce the amount of B7 available for binding to CD28. In either case, it appears that CTLA-4, CD28, and B7 each play an important role in the intricate regulation of T-cell proliferation.

SUMMARY OF THE INVENTION

The present invention relates to peptides which bind to CTLA-4 and which co-stimulate T-cell proliferation. The peptides of the invention, which include monoclonal antibodies, functionally active antibody fragments and functionally active polypeptides, specifically interact with human CTLA-4 and prevent the interaction of B7 with human CTLA-4.

These peptides have particular utility as pharmaceuticals for the immunotherapy of T-cell proliferation sensitive disorders because of their ability to co-stimulate T-cell proliferation. The peptides of the invention are particularly effective for immunotherapy of T-cell proliferation sensitive disorders when administered in combination with conventional therapeutics used for the treatment of such disorders. For instance a tumor, which is a T-cell proliferation sensitive disorder, is conventionally treated with a chemotherapeutic agent which functions by killing rapidly dividing cells. The peptides of the invention when administered in conjunction with a chemotherapeutic agent enhance the tumoricidal effect of the chemotherapeutic agent by stimulating T-cell proliferation to enhance the immunological rejection of the tumor cells.

A major advantage of the peptides of the invention derives from the fact that they specifically interact with human CTLA-4. Because the peptides of the invention interact specifically with human CTLA-4 they may be used in vivo in humans to co-stimulate T-cell proliferation. The in vivo enhancement of T-cell proliferation is desirable as an aid in the treatment of many of T-cell proliferation sensitive disorders of the immune system, such as diseases resulting from immunodeficiency, as well as disorders involving unwanted cellular invasion or growth, such as invasion of the body by foreign microorganisms or tumor growth.

In particular, the present invention provides a composition of a peptide that selectively binds to human CTLA-4 and co-stimulates T-cell proliferation. In one embodiment the peptide has a CTLA-4 binding CDR3 region. The CTLA-4 binding CDR3 region may be a $CDR3_{A3.4H2}$ or functional variant thereof of a monoclonal antibody produced by hybridoma A3.4H2 deposited under ATCC Accession No. HB-12319. In another embodiment the CTLA-4 binding CDR3 region is a $CDR3_{A3.6B10}$ or functional variant thereof of a monoclonal antibody produced by hybridoma A3.6B10 deposited under ATCC Accession No. HB-12318.

The peptide may be an intact soluble monoclonal antibody. According to one embodiment of the invention the peptide is an intact soluble monoclonal antibody$_{A3.4H2}$ produced by the hybridoma cell line deposited under ATCC Accession No.HB-12319 or an intact antibody having the binding characteristics of the deposited monoclonal antibody. In another embodiment the peptide is an intact soluble monoclonal antibody$_{A3.6B10}$ produced by the hybridoma cell line deposited under ATCC Accession No. HB-12318 or an intact antibody having the binding characteristics of the deposited monoclonal antibody. According to yet another embodiment the peptide is a humanized monoclonal antibody.

The peptide also may be a functionally active monoclonal antibody fragment or a functionally active polypeptide. In one embodiment the peptide is a monoclonal antibody fragment selected from the group consisting of an F(ab')$_2$ fragment, an Fd fragment, and an Fab fragment. In another embodiment the peptide has a light chain CDR2 region selected from the group consisting of a CDR2$_{A3.4H2}$ or functional variant thereof of a monoclonal antibody produced by hybridoma A3.4H2 deposited under ATCC Accession No. HB-12319 and a CDR2$_{A3.6B10}$ or functional variant thereof of a monoclonal antibody produced by hybridoma A3.6B10 deposited under ATCC Accession No. HB-12318. According to another embodiment the peptide has a light chain CDR1 region selected from the group consisting of a CDR1$_{A3.4H2}$ or functional variant thereof of a monoclonal antibody produced by hybridoma A3.4H2 deposited under ATCC Accession No. HB-12319 and a CDR1$_{A3.6B10}$ or functional variant thereof of a monoclonal antibody produced by hybridoma A3.6B10 deposited under ATCC Accession No. HB-12318.

A pharmaceutical composition for treating a human T-cell proliferation sensitive disorder is provided according to another aspect of the invention. The pharmaceutical composition includes an effective amount for treating the human T-cell proliferation sensitive disorder of a peptide that selectively binds to human CTLA-4 and that co-stimulates T-cell proliferation and a pharmaceutically acceptable carrier. In one embodiment the peptide has a CTLA-4 binding CDR3.

According to one embodiment of the invention the CTLA-4 binding CDR3 region is a CDR3$_{A3.4}$H2 or functional variant thereof of a monoclonal antibody produced by hybridoma A3.4H2 deposited under ATCC Accession No. HB-12319. In another embodiment the CTLA-4 binding CDR3 region is a CDR3$_{A3.6B10}$ or functional variant thereof a monoclonal antibody produced by hybridoma A3.6B10 deposited under ATCC Accession No. HB-12318.

The peptide may be an intact soluble monoclonal antibody. According to one embodiment of the invention the peptide is an intact soluble monoclonal antibody$_{A3.4H2}$ produced by the hybridoma cell line deposited under ATCC Accession No. HB12319 or an intact antibody having the binding characteristics of the deposited monoclonal antibody. In another embodiment the peptide is an intact soluble monoclonal antibody$_{A3.6B10}$ produced by the hybridoma cell line deposited under ATCC Accession No. HB-12318 or an intact antibody having the binding characteristics of the deposited monoclonal antibody. According to yet another embodiment the peptide is a humanized monoclonal antibody.

The peptide also may be a functionally active monoclonal antibody fragment or a functionally active polypeptide. In one embodiment the peptide is a monoclonal antibody fragment selected from the group consisting of an F(ab')$_2$ fragment, an Fd fragment, and an Fab fragment. In another embodiment the peptide has a light chain CDR2 region selected from the group consisting of a CDR2$_{A3.4H2}$ or functional variant thereof of a monoclonal antibody produced by hybridoma A3.4H2 deposited under ATCC Accession No. HB-12319 and a CDR2$_{A3.6B10}$ or functional variant thereof of a monoclonal antibody produced by hybridoma A3.6B10 deposited under ATCC Accession No. HB-12318. According to another embodiment the peptide has a light chain CDR1 region selected from the group consisting of a CDR1$_{A3.4H2}$ or functional variant thereof of a monoclonal antibody produced by hybridoma A3.4H2 deposited under ATCC Accession No. HB-12319 and a CDR1$_{A3.6B10}$ or finctional variant thereof of a monoclonal antibody produced by hybridoma A3.6B10 deposited under ATCC Accession No. HB-12318.

The present invention further provides a method of stimulating T-cell proliferation in situ. The method involves the step of adding a peptide that binds to human CTLA-4 to a population of cells including T-cells and antigen presenting cells to co-stimulate T-cell proliferation. In one embodiment the peptide has a CTLA-4 binding CDR3 region.

According to another aspect of the invention a method of treating a T-cell proliferation sensitive disorder is provided. The method involves the step of administering to a subject having a T-cell proliferation sensitive disorder a peptide that binds to human CTLA-4 in an amount effective to increase T-cell proliferation. In one embodiment the peptide has a CTLA-4 binding CDR3 region. In another embodiment the T-cell proliferation sensitive disorder is a tumor. In another embodiment the T-cell proliferation sensitive disorder is an immunodeficiency disease.

The present invention also provides antibody producing hybridomas having ATCC Accession No. HB-12318 and ATCC Accession No. HB-12319. These hybridomas produce the antibodies having the CDR3 region which specifically interacts with CTLA-4 and co-stimulates T-cell proliferation.

According to another aspect of the invention a nucleic acid molecule is provided. In one embodiment the nucleic acid molecule is the nucleic acid sequence of the antibodies produced by the deposited hybridomas. Each of the deposited hybridomas enable the production of the nucleic acid molecules of the invention because it is within the routine skill of the ordinary artisan to isolate and sequence DNA from an established cell line. According to another embodiment the nucleic acid molecule is selected from the group consisting of intact monoclonal antibodies that selectively bind to human CTLA-4, humanized antibodies that selectively bind to human CTLA-4, antibody fragments that selectively bind to human CTLA-4, and CDR regions that selectively bind to human CTLA-4.

DETAILED DESCRIPTION OF THE INVENTION

The invention involves the finding that specific peptides, which bind to human CTLA-4 on T-cells and inhibit B7 molecules from binding to CTLA-4, co-stimulate the proliferation of T-cells. By stimulating T-cell proliferation the peptides of the invention are useful for enhancing an immune response in vivo which may be useful for the treatment of many disorders which related to immune function. The peptides can be used alone as a primary therapy or in combination with other therapeutics as an adjuvant therapy to enhance the therapeutic benefits of other medical treatments. The peptides of the invention are useful typically when it is desirable to co-stimulate T-cell proliferation.

As is well-known in the art, the complementarity determining regions (CDRs) of an antibody are the portions of the antibody which are largely responsible for antibody specificity. The CDR's directly interact with the epitope of the antigen (see, in general, Clark, 1986; Roitt, 1991). In both the heavy chain and the light chain variable regions of IgG immunoglobulins, there are four framework regions (FR1 through FR4) separated respectively by three complementarity determining regions (CDR1 through CDR3). The framework regions (FRs) maintain the tertiary structure of the paratope, which is the portion of the antibody which is involved in the interaction with the antigen. The CDRs, and in particular the CDR3 regions, and more particularly the heavy chain CDR3 contribute to antibody specificity. Because these CDR regions and in particular the CDR3 region confer antigen specificity on the antibody these regions may be incorporated into other antibodies or peptides to confer the identical antigen specificity onto that antibody or peptide.

The present invention encompasses peptides including a CTLA-4 binding region which specifically binds to human CTLA-4 and prevents CTLA-4 from interacting with B7. Optionally the CTLA-4 binding region is a CTLA-4 binding CDR3 region. CTLA-4 is a T-cell surface receptor protein. "B7" as used herein is a family of structurally related glycoprotiens which include B7-1, B7-2, and B7-3. A "CTLA-4 binding CDR3 region" as used herein is a CDR3 peptide sequence derived from the monoclonal antibodies produced by the hybridomas deposited with the ATCC under ATCC Accession No. HB-12318 and ATCC Accession No. HB-12319.

Two antibody producing hybridoma cell lines (A3.4H2 and A3.6B10) were deposited by Applicants with the ATCC on Mar. 21, 1997. Hybridoma A3.4H2 produces monoclonal antibody$_{A3.4H2}$ having binding specificity for CTLA-4. Monoclonal antibody$_{A3.4H2}$ includes the CDR3$_{A3.4H2}$ region within its sequence. As used herein "CDR3$_{A3.4H2}$" includes the CDR3 region of monoclonal antibody$_{A3.4H2}$. Hybridoma A3.6B10 produces monoclonal antibody$_{A3.6B10}$ having binding specificity for CTLA-4. Monoclonal antibody$_{A3.6B10}$ includes the CDR3$_{A3.6B10}$ region within its sequence. As used herein "CDR3$_{A3.6B10}$" includes the CDR3 region of monoclonal antibody$_{A3.6B10}$. Both monoclonal antibody$_{A3.4H2}$ and monoclonal antibody$_{A3.6B10}$ specifically bind to CTLA-4 and prevent CTLA-4 from interacting with B7.

The "CTLA-4 binding CDR3 region" refers to the CDR3$_{A3.4H2}$ and CDR3$_{A3.6B10}$ peptide sequences. In one embodiment of the invention peptides of the invention include functional variants of the CTLA-4 binding CDR3 region. A "functional variant" as used herein is a peptide having the sequence of the CDR3$_{A3.4H2}$ or CDR3$_{A3.6B10}$ regions with conservative substitutions therein. As used herein, "conservative substitution" refers to an amino acid substitution which does not alter the relative charge or size characteristics of the peptide in which the amino acid substitution is made. Conservative substitutions of amino acids include substitutions made amongst amino acids with the following groups: (1) M,I,L,V; (2) F,Y,W; (3) K,R,H; (4) A,G; (5) S,T; (6) Q,N; and, (7) E,D. Such substitutions can be made by a variety of methods known to one of ordinary skill in the art. For example, amino-acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding the CDR3 region. These and other methods for altering a CDR3 region peptide will be known to those of ordinary skill in the art and may be found in references which compile such methods, e.g. Sambrook or Ausubel, noted above. The activity of functionally equivalent variants of the CTLA-4 binding CDR3 region can be tested by the binding and activity assays discussed in more detail below.

For purposes of brevity the term "ATCC deposited hybridoma" is used throughout the specification to refer to both of the hybridomas deposited with the ATCC on Mar. 21, 1997. The term "deposited monoclonal antibody" is used to refer to both of the monoclonal antibodies (monoclonal antibody$_{A3.4H2}$ or monoclonal antibody$_{A3.6B10}$) produced by the ATCC deposited hybridomas. For purposes of definiteness in the attached claims each of the hybridomas and monoclonal antibodies is specifically recited.

As used herein the term "peptide" includes monoclonal antibodies, functionally active antibody fragments, and functionally active polypeptides.

The peptides of the invention are isolated peptides. As used herein, with respect to peptides, the term "isolated peptides" means that the peptides are substantially pure and are essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems.

According to one embodiment, the peptide of the invention is an intact soluble anti-CTLA-4 monoclonal antibody in an isolated form or in a pharmaceutical preparation. An intact soluble monoclonal antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains are further divided unto subregions referred to as variable regions and constant regions. As used herein the term "monoclonal antibody" refers to a homogenous population of immunoglobulins which specifically bind to an epitope (i.e. antigenic determinant) of human CTLA-4.

The peptide of the invention in one embodiment is, for example, the deposited monoclonal antibody. The preparation and use of the deposited monoclonal antibody is described more fully in the attached Examples. In another embodiment the peptide of the invention is an intact antibody having the binding characteristics of the deposited monoclonal antibody. An antibody having the binding characteristics of the deposited monoclonal antibody is one which binds to CTLA-4 and inhibits CTLA-4 from interacting with B7. One of ordinary skill in the art can easily identify antibodies having the binding characteristics of the deposited monoclonal antibody using the screening and binding assays set forth in detail below.

In one set of embodiments, the peptide useful according to the methods of the present invention is an intact humanized anti-CTLA-4 monoclonal antibody in an isolated form or in a pharmaceutical preparation. The following examples of methods for preparing humanized monoclonal antibodies that interact with CTLA-4 and co-stimulate the activation of T-cells are exemplary and are provided for illustrative purposes only.

A "humanized monoclonal antibody" as used herein is a human monoclonal antibody or functionally active fragment thereof having human constant regions and a CTLA-4 binding CDR3 region from a mammal of a species other than a human. Humanized monoclonal antibodies may be made by any method known in the art. Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View Calif.).

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector including a suitable promoter operably linked to a DNA sequence encoding at least a variable domain of an Ig heavy or light chain and the variable domain comprising framework regions from a human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vectors. Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. (Preferred vectors and recombinant techniques are discussed in greater detail below.) For example, the DNA sequence encoding the domain may be prepared by oligonucleotide synthesis. Alternatively a synthetic gene lacking the CDR regions in which four framework regions are fused together with suitable restriction sites at the junctions, such that double stranded synthetic or restricted subcloned CDR cassettes with sticky ends could be ligated at the junctions of the framework regions. Another method involves the preparation of the DNA sequence encoding the variable CDR containing domain by oligonucleotide site-directed mutagenesis. Each of these methods is well known in the art. Therefore, those skilled in the art may construct humanized antibodies containing a murine CDR region without destroying the specificity of the antibody for its epitope.

In preferred embodiments, the humanized antibodies of the invention are human monoclonal antibodies including at least the CTLA-4 binding CDR3 region of the deposited monoclonal antibody. As noted above, such humanized antibodies may be produced in which some or all of the FR regions of deposited monoclonal antibody have been replaced by homologous human FR regions. In addition, the Fc portions may be replaced so as to produce IgA or IgM as well as human IgG antibodies bearing some or all of the CDRs of the deposited monoclonal antibody. Of particular importance is the inclusion of the deposited monoclonal antibody CTLA-4 binding CDR3 region and, to a lesser extent, the other CDRs and portions of the framework regions of the deposited monoclonal antibody. Such humanized antibodies will have particular clinical utility in that they will specifically recognize human CTLA-4 but will not evoke an immune response in humans against the antibody itself. In a most preferred embodiment, a murine CDR is grafted into the framework region of a human antibody to prepare the "humanized antibody." See, e.g., L. Riechmann et al., Nature 332, 323 (1988); M. S. Neuberger et al., Nature 314, 268 (1985) and EPA 0 239 400 (published Sep. 30, 1987).

In one embodiment of the invention the peptide containing a CTLA-4 binding region is a functionally active antibody fragment. Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. An isolated $F(ab')_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', $F(ab')_2$ and Fv are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)].

As used herein the term "functionally active antibody fragment" means a fragment of an antibody molecule including a CTLA-4 binding region of the invention which retains the T-cell stimulating functionality of an intact antibody having the same specificity such as the deposited monoclonal antibodies. Such fragments are also well known in the art and are regularly employed both in vitro and in vivo. In particular, well-known functionally active antibody fragments include but are not limited to $F(ab')_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316–325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644–646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevieer, Amsterdam, 1985)), Fv fragments (Hochman et al., Biochemistry 12: 1130 (1973); Sharon et al., Biochemistry 15: 1591 (1976); Ehrilch et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies for the CTLA-4 epitope.

Functionally active antibody fragments also encompass "humanized antibody fragments." As one skilled in the art will recognize, such fragments could be prepared by traditional enzymatic cleavage of intact humanized antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin fragment.

Smaller antibody fragments and small binding polypeptides having binding specificity for CTLA-4 also are embraced within the peptides of the present invention. Several routine assays may be used to easily identify such peptides. Screening assays for identifying peptides of the invention are performed for example, using phage display procedures such as those described in Hart, et al., *J. Biol. Chem.* 269:12468 (1994). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Ligands that bind selectively to CTLA-4 are obtained by selecting those phages which express on their surface a ligand that binds to CTLA-4. These phages then are subjected to several cycles of reselection to identify the peptide ligand-expressing phages that have the most useful binding characteristics. Typically, phages that exhibit the best binding characteristics (e.g., highest affinity) are further characterized by nucleic acid analysis to identify the particular amino acid sequences of the peptides expressed on the phage surface and the optimum length of the expressed peptide to achieve optimum binding to CTLA-4. Alternatively, such peptide ligands can be selected from combinatorial libraries of peptides containing one or more amino acids. Such libraries can further be synthesized which contain non-peptide synthetic moieties which are less subject to enzymatic degradation compared to their naturally-occurring counterparts.

Additionally small polypeptides including those containing the CTLA-4 binding CDR3 region may easily be synthesized or produced by recombinant means to produce the peptide of the invention. Such methods are well known to those of ordinary skill in the art. Peptides can be synthesized for example, using automated peptide synthesizers which are commercially available. The peptides can be produced by recombinant techniques by incorporating the DNA expressing the peptide into an expression vector and transforming cells with the expression vector to produce the peptide.

The sequence of the CDR regions, for use in synthesizing the peptides of the invention, may be determined by methods known in the art. The heavy chain variable region is a peptide which generally ranges from 100 to 150 amino acids in length. The light chain variable region is a peptide which generally ranges from 80 to 130 amino acids in length. The CDR sequences within the heavy and light chain variable regions which include only approximately 3–25 amino acid sequences may easily be sequenced by one of ordinary skill in the art. The peptides may even be synthesized by commercial sources such as by the Scripps Protein and Nucleic Acids Core Sequencing Facility (La Jolla Calif.).

To determine whether a peptide binds to CTLA-4 any known binding assay may be employed. For example, the peptide may be immobilized on a surface and then contacted with a labeled CTLA-4. The amount of CTLA-4 which interacts with the peptide or the amount which does not bind to the peptide may then be quantitated to determine whether the peptide binds to CTLA-4. A surface having the deposited monoclonal antibody immobilized thereto may serve as a positive control.

Screening of peptides of the invention, also can be carried out utilizing a competition assay. If the peptide being tested competes with the deposited monoclonal antibody, as shown by a decrease in binding of the deposited monoclonal antibody, then it is likely that the peptide and the deposited monoclonal antibody bind to the same, or a closely related, epitope. Still another way to determine whether a peptide has the specificity of the deposited monoclonal antibody of the invention is to pre-incubate the deposited monoclonal antibody with CTLA-4 with which it is normally reactive, and then add the peptide being tested to determine if the peptide being tested is inhibited in its ability to bind CTLA-4. If the peptide being tested is inhibited then, in all likelihood, it has the same, or a functionally equivalent, epitope and specificity as the deposited monoclonal antibody.

Using routine procedures known to those of ordinary skill in the art, one can determine whether a peptide which binds to CTLA-4 is useful according to the invention by determining whether the peptide is one which blocks CTLA-4 from binding to B7 and co-stimulates T-cell proliferation in an in vitro assay. A peptide which co-stimulates T-cell proliferation is one which when added to a T-cell results in a secondary signal stimulating proliferation of the T-cell or the production of soluble immune mediators by the T-cell when the T-cell is exposed to a primary signal, such as that caused by antigen in the context of MHC on the surface of an APC.

An example of a T-cell proliferation assay is disclosed in Walunas et al., *J. Exp. Med V.* 183, p. 2541–2550 (1996). Briefly, lymph node cells are isolated and enriched for T-cells by passage over a nylon wool column and T-cell purity is evaluated by flow cytometry using an anti-CD3 monoclonal antibody. The T-cells are plated at a density of $2 \times 10^5$/well in the presence of $1 \times 10^5$ irradiated syngeneic, erythrocyte-depleted B6 splenocytes. Once the cells are prepared, two assay conditions are set up. A first assay condition involves incubating the T-cell mixture with 0.1 mg/ml of anti-CD3 and 1.0 mg/ml of anti-CD28 for 72 hours at 37. The second assay condition involves incubating the T-cell mixture with 0.1 mg/ml of anti-CD3 alone for 72 hours at 37. Each of the assay conditions are mixed with either control Ig (50 mg/ml), anti-CTLA-4 (50 mg/ml) (such as the deposited monoclonal antibody), or the test peptide of the invention (50 mg/ml). During the last 16 hours of the incubation the mixture is pulsed with 1 mCi/well [$^3$H] thymidine. The samples are then counted on a scintillation counter and the proliferation of the cells is measured as a function of the [$^3$H] thymidine incorporated into the cells.

Other assays will be apparent to those of skill in the art, having read the present specification, which are useful for determining whether a peptide which binds to CTLA-4 also co-stimulates T-cell activation.

By using the deposited monoclonal antibody of the invention, it is now possible to produce anti-idiotypic antibodies which can be used to screen other antibodies to identify whether the antibody has the same binding specificity as the deposited monoclonal antibody of the invention. In addition, such anti-idiotypic antibodies can be used for active immunization (Herlyn, et al., Science, 232:100, 1986). Such anti-idiotypic antibodies can be produced using well-known hybridoma techniques (Kohler and Milstein, Nature, 256:495, 1975). An anti-idiotypic antibody is an antibody which recognizes unique determinants present on the deposited monoclonal antibody. These determinants are located in the hypervariable region of the antibody. It is this region which binds to a given epitope and, thus, is responsible for the specificity of the antibody. An anti-idiotypic antibody can be prepared by immunizing an animal with the deposited monoclonal antibody. The immunized animal will recognize and respond to the idiotypic determinants of the immunizing deposited monoclonal antibody and produce an antibody to these idiotypic determinants. By using the anti-idiotypic antibodies of the immunized animal, which are specific for the deposited monoclonal antibody of the invention, it is possible to identify other clones with the same idiotype as the deposited monoclonal antibody used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody. Thus, the anti-idiotypic monoclonal antibody can be used for immunization, since the anti-idiotype monoclonal antibody binding domain effectively acts as an antigen.

Each of the above-described compositions includes a peptide having a CTLA-4 binding region. As discussed above, the variable region of an antibody which includes the CDR3 region is responsible for the specificity of the antibody.

The sequences responsible for the specificity of the deposited monoclonal antibody can easily be determined by one of ordinary skill in the art so that peptides according to the invention can be prepared using recombinant DNA technology. There are entities in the United States which will perform this function commercially, such as Thomas Jefferson University and the Scripps Protein and Nucleic Acids Core Sequencing Facility (La Jolla Calif.). For example, the variable region cDNA can be prepared by polymerase chain reaction from the deposited hybridoma RNA using degenerate or non-degenerate primers (derived from the amino acid sequence). The cDNA can be subcloned to produce sufficient quantities of double stranded DNA for sequencing by conventional sequencing reactions or equipment. These procedures are set forth in detail in the attached Examples.

Once the nucleic acid sequences of the heavy chain Fd and light chain variable domains of the deposited CTLA-4 monoclonal antibody are determined, one of ordinary skill in the art is now enabled to produce nucleic acids which encode this antibody or which encode the various antibody fragments, humanized antibodies, or polypeptides described above. It is contemplated that such nucleic acids will be operably joined to other nucleic acids forming a recombinant vector for cloning or for expression of the peptides of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the CDR3 region and additional variable sequences contributing to the specificity of the antibodies or parts thereof, as well as other non-specific peptide sequences and a suitable promoter either with (Whittle et al., Protein Eng. 1:499, 1987 and Burton et al., Science 266:1024–1027, 1994) or without (Marasco et al., Proc. Natl. Acad. Sci. (USA) 90:7889, 1993 and Duan et al., Proc. Natl. Acad. Sci. (USA) 91:5075–5079,1994) a signal sequence for export or secretion. Such vectors may be transformed or transfected into prokaryotic (Huse et al., Science 246:1275, 1989, Ward et al., Nature 341: 644–646, 1989; Marks et al., J. Mol. Biol. 222:581, 1991 and Barbas et al., Proc. Natl. Acad. Sci. (USA) 88:7978, 991) or eukaryotic (Whittle et al., 1987 and Burton et al., 1994) cells or used for gene therapy (Marasco et al., 1993 and Duan et al., 1994) by conventional techniques, known to those with skill in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

The expression vectors of the present invention include regulatory sequences operably joined to a nucleotide sequence encoding one of the peptides of the invention. As used herein, the term "regulatory sequences" means nucleotide sequences which are necessary for or conducive to the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the peptides may be accomplished by any of a variety of standard means known in the art.

A preferred vector for screening peptides, but not necessarily preferred for the mass production of the peptides of the invention, is a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of the invention, and, optionally, (3) a fusion protein domain. The vector includes DNA regulatory sequences for expressing the fusion polypeptide, preferably prokaryotic regulatory sequences. Such vectors can be constructed by those with skill in the art and have been described by Smith et al. (*Science* 228:1315–1317, 1985), Clackson et al. (*Nature* 352:624–628, 1991); Kang et al. (in "Methods: A Companion to Methods in Enzymology: Vol. 2", R. A. Lerner and D. R. Burton, ed. Academic Press, NY, pp 111–118,1991); Barbas et al. (*Proc. Natl. Acad. Sci.* (*USA*) 88:7978–7982, 1991), Roberts et al. (*Proc. Natl. Acad. Sci.* (*USA*) 89:2429–2433, 1992)

A fusion polypeptide may be useful for purification of the peptides of the invention. The fusion domain may, for example, include a poly-His tail which allows for purification on Ni+ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies. The filamentous phage membrane anchor is preferably a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein membrane of the host cell, such as the periplasmic membrane of gram negative bacteria. A preferred secretion signal for *E. coli* is a pelB secretion signal. The predicted amino acid residue sequences of the secretion signal domain from two pelB gene producing variants from *Erwinia carotova* are described in Lei, et al. (*Nature* 381:543–546, 1988). The leader sequence of the pelB protein has previously been used as a secretion signal for fusion proteins (Better, et al., *Science* 240:1041–1043, 1988; Sastry, et al., *Proc. Natl. Acad. Sci* (*USA*) 86:5728–5732, 1989; and Mullinax, et al., *Proc. Natl. Acad. Sci.* (*USA*) 87:8095–8099, 1990). Amino acid residue sequences for other secretion signal polypeptide domains from *E. coli* useful in this invention can be found in Oliver, In Neidhard, F.C. (ed.), *Escherichia coli* and *Salmonella Typhimurium*, American Society for Microbiology, Washington, D.C., 1:56–69 (1987).

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3–9 nucleotides long located 3–11 nucleotides upstream from the initiation codon (Shine, et al., *Nature* 254:34, 1975). The sequence, AGGAGGU, which is called the Shine-Dalgarno (SD) sequence, is complementary to the 3' end of *E. coli* 16S rRNA. Binding of the ribosome to mRNA and the sequence at the 3' end of the mRNA can be affected by several factors:

(I) The degree of complementarity between the SD sequence and 3' end of the 16S rRNA.

(ii) The spacing and possibly the DNA sequence lying between the SD sequence and the AUG (Roberts, et al., *Proc. Natl. Acad. Sci.* (*USA*) 76:760.,1979a: Roberts, et al., *Proc. Natl. Acad. Sci.* (*USA*) 76:5596, 1979b; Guarente, et al., *Science* 209:1428, 1980; and Guarente, et al., *Cell* 20:543, 1980). Optimization is achieved by measuring the level of expression of genes in plasmids in which this spacing is systematically altered. Comparison of different mRNAs shows that there are statistically preferred sequences from positions −20 to +13 (where the A of the AUG is position 0) (Gold, et al., *Annu. Rev. Microbiol.* 35:365, 1981). Leader sequences have been shown to influence translation dramatically (Roberts, et al., 1979a, b supra).

(iii) The nucleotide sequence following the AUG, which affects ribosome binding (Taniguchi, et al., *J. Mol. Biol.*, 118:533, 1978).

The 3' regulatory sequences define at least one termination (stop) codon in frame with and operably joined to the heterologous fusion polypeptide.

In preferred embodiments with a prokaryotic expression host, the vector utilized includes a prokaryotic origin of replication or replicon, i.e., a DNA sequence having the ability to direct autonomous replication and maintenance of the recombinant DNA molecule extrachromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColE1 found in pBR322 and a variety of other common plasmids. Also preferred is the p15A origin of replication found on pACYC and its derivatives. The ColE1 and p15A replicons have been extensively utilized in molecular biology, are available on a variety of plasmids and are described by Sambrook. et al., *Molecular Cloning: A Laboratory Manual,* 2nd edition, Cold Spring Harbor Laboratory Press, 1989).

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as pcDNAII available from Invitrogen, (San Diego, Calif.).

When the peptide of the invention is an antibody including both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the intact antibodies of the invention or the $F(ab')_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a dicistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody polypeptide that is produced when an insert translatable DNA sequence (insert DNA) is directionally inserted into the cassette via the sequence of nucleotides adapted for directional ligation.

The dicistronic expression vector also contains a second cassette for expressing the second antibody polypeptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

The peptides of the present invention may also, of course, be produced by eukaryotic cells such as CHO cells, human hybridomas, immortalized B-lymphoblastoid cells, and the like. In this case, a vector is constructed in which eukaryotic regulatory sequences are operably joined to the nucleotide sequences encoding the peptide. The design and selection of an appropriate eukaryotic vector is within the ability and discretion of one of ordinary skill in the art. The subsequent purification of the peptides may be accomplished by any of a variety of standard means known in the art.

In another embodiment, the present invention provides host cells, both prokaryotic and eukaryotic, transformed or transfected with, and therefore including, the vectors of the present invention.

As used herein with respect to nucleic acids, the term "isolated" means: (I) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

The peptides can also be used immunotherapeutically for T-cell proliferation sensitive disorders in humans. The term, "immunotherapeutically" or "immunotherapy" as used herein in conjunction with the monoclonal antibodies of the invention denotes both prophylactic as well as therapeutic administration. Thus, the peptides can be administered to high-risk subjects in order to lessen the likelihood and/or severity of a T-cell proliferation sensitive disease, such as a tumor or administered to subjects already evidencing tumors.

In one aspect the invention encompasses a method for stimulating T-cell proliferation in situ. The method involves the step of adding a peptide of the invention to a population of cells including T-cells and antigen presenting cells. As used herein "T-cells" refer to T-cells expressing CTLA-4 and CD28 on the surface thereof and "antigen presenting cells" refers to any immune cell expressing B7 and presenting an antigen in the context of MHC on the surface. When a peptide of the invention is added to a population of T-cells and antigen presenting cells the peptide interacts with CTLA-4 preventing the CTLA-4 from interacting with B7 on the surface of the antigen presenting cell. The antigen presenting cell is then free to interact with the T-cell to generate a primary and secondary signal resulting in T-cell proliferation.

By definition, the word "in-situ" encompasses and includes the terms "in-vivo", "ex-vivo" and "in-vitro." The compositions of the invention are useful for many in vitro purposes. For example, the compositions of the invention are useful for screening compounds which inhibit T-cell proliferation. Such a screening assay may be performed in vitro by setting up cell proliferation assays including a peptide of the invention and a population of cells including T-cells and antigen presenting cells. Potential T-cell proliferation inhibitors may be added to the mixture and the effect on proliferation may be measured. Other in vitro uses, such as research purposes, are known to those of ordinary skill in the art.

Ex-vivo uses also will be easily identified by those of skill in the art. Ex-vivo uses include, for example, the stimulation of proliferation of T-cells which have been removed from a human subject and which are subsequently returned to the body of the human subject. Ex-vivo uses are useful when other ex-vivo procedures are being performed on a subject and when it is desirable to separate the T-cells from other components of the blood before manipulation.

The present invention also includes a method for treating a T-cell proliferation sensitive disorder. The method involves the step of administering a peptide of the invention to a subject having a T-cell proliferation sensitive disorder in an amount effective to increase T-cell proliferation.

A "T-cell proliferation sensitive disorder" as used herein is any disorder associated with adverse physiological consequences in which an enhancement of immune cell function, embodied by an increase in T-cell proliferation, results in an improvement of the adverse physiological consequences. T-cell proliferation sensitive disorders include disorders of the immune system, such as immunodeficiency, as well as disorders involving undesirable cellular invasion by microorganisms or undesirable cell growth such as tumors.

The peptide of the invention is a secondary co-stimulatory signal which requires a primary co-stimulatory event to initiate T-cell proliferation. The primary co-stimulatory event may be the interaction of a T-cell with an antigen in the context of MHC. When a T-cell has been exposed to an antigen in the context of MHC it is not necessary to add an additional primary co-stimulatory signal, when the secondary co-stimulatory signal is added, in order to stimulate proliferation of the cell. For example, when the peptide of the invention is administered to a human subject infected with a particular antigen or expressing a particular antigen on a tumor cell such that the antigen is incorporated into and expressed on the surface of circulating APCs, it is not necessary to administer a primary co-stimulatory signal in order to stimulate T-cell proliferation. The antigen presented on the surface of the circulating APCs of the subject function as a primary co-stimulatory signal.

When antigen is not expressed on the surface of circulating APCs a primary co-stimulatory signal may be administered in conjunction with the secondary co-stimulation signal (the peptide of the invention). For example, an antigen may not be expressed on the surface of circulating APCs of a subject when that subject has not been exposed to a particular infectious agent. It might be desirable to stimulate T-cell proliferation in such a subject when the subject may be exposed to the infectious agent in the future. Stimulating T-cell proliferation under such conditions enhances the immunity of the subject to the particular infectious agent when the subject is exposed to it in the future.

The compositions of the invention are administered in therapeutically effective amounts. As used herein, an "effective amount" of the peptide of the invention is a dosage which is sufficient to inhibit B7 from binding to CTLA-4 to an extent which will co-stimulate T-cell proliferation. Stimulating T-cell proliferation is sufficient to produce the desired effect in which the symptoms associated with T-cell proliferation sensitive disorder are ameliorated or decreased. Preferably an effective amount of the peptide is an effective amount for promoting T-cell proliferation in vivo. Generally, a therapeutically effective amount may vary with the subject's age, condition, and sex, as well as the extent of the disease in the subject and can be determined by one of skill in the art. The dosage may be adjusted by the individual physician in the event of any complication. A therapeutically effective amount typically will vary from about 0.01 mg/kg to about 500 mg/kg, were typically from about 0.1 mg/kg to about 200 mg/kg, and often from about 0.2 mg/kg to about 20 mg/kg, in one or more dose administrations daily, for one or several days (depending of course of the mode of administration and the factors discussed above).

One of skill in the art can determine what an effective amount of a peptide is by screening the ability of the peptide to inhibit the activation of T-cell proliferation in an in vitro assay. The affectivity of the peptide can be defined in terms of the ability of the peptide to inhibit T-cell proliferation. An exemplary assay for measuring the ability of a putative peptide of the invention to inhibit T-cell proliferation is provided in the Examples and has been discussed above. The exemplary assay is predictive of the ability of a peptide to co-stimulate T-cell proliferation in vivo and, hence, can be used to select peptides for therapeutic applications. The proliferation assay measures the ability of a peptide to co-stimulate T-cell proliferation.

According to the methods of the invention, the peptide may be administered in a pharmaceutically acceptable composition. In general, pharmaceutically-acceptable carriers for monoclonal antibodies, antibody fragments, and peptides are well-known to those of ordinary skill in the art. As used herein, a pharmaceutically-acceptable carrier means a nontoxic material that does not interfere with the effectiveness of the biological activity of the active ingredients, i.e., the ability of the peptide to co-stimulate T-cell activation. Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. The peptides of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

According to the methods of the invention the peptides can be administered by injection, by gradual infusion over time or by any other medically acceptable mode. The administration may, for example, be intravenous, intraperitoneal, intramuscular, intracavity, subcutaneous or transdermal. Preparations for parenteral administration includes sterile aqueous or nonaqueous solutions, suspensions and emulsions. Examples of nonaqueous solvents are propylene glycol, polyethylene glycol, vegetable oil such as olive oil, an injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents, and inert gases and the like. Those of skill in the art can readily determine the various parameters for preparing these alternative pharmaceutical compositions without resort to undue experimentation.

The methods of the invention also encompass the step of administering the peptides of the invention in conjunction with conventional therapies for treating the underlying T-cell proliferation sensitive disorder. For example, the method of the invention may be practiced simultaneously with the conventional treatment. The particular conventional treatment depends of course on the nature of the T-cell proliferation sensitive disorder. When, for example, the T-cell proliferation sensitive disorder is a tumor, a conventional mode of treatment is chemotherapy. The peptides of the invention may be administered in conjunction with chemotherapy in the treatment of the tumor in order to provide enhanced tumoricidal effects.

The following examples are provided to illustrate specific instances of the practice of the present invention and are not to be construed as limiting the present invention to these examples. As will be apparent to one of ordinary skill in the art, the present invention will find application in a variety of compositions and methods.

EXAMPLES

Example 1

Preparation of Anti-CTLA-4 Monoclonal Antibody Producing Hybridomas

1. Immunization

BALB/c female mice (Jackson Laboratories, Bar Harbor, Me.) were immunized by a combination of subcutaneous (3 different sites) and intraperitoneal injection with $10^7$ activated human T cell clones suspended in Dulbecco's phosphate buffered saline, then emulsified with an equal volume of complete Freund's adjuvant (Sigma Chemical Co., St. Louis, Mo.). The mice were given two intraperitoneal booster immunizations of $10^7$ activated human T cell clones suspended in Dulbecco's phosphate buffered saline (GIBCO, Grand Island, N.Y.), then emulsified with an equal volume of incomplete Freund's adjuvant (Sigma Chemical Co., St. Louis, Mo.) at 14 day intervals following the initial immunization.

2. Screening of Mice with Flow Cytometry

The presence of antibodies to surface proteins on T cell clones was tested by flow cytometry. Ten days following the third and final immunization, a small amount of blood was collected by retro-orbital bleed from each mouse and clotted. Activated T cell clones grown in tissue culture flasks were collected and washed thoroughly (3x) with 1% bovine serum albumin dissolved in Dulbecco's phosphate buffered saline (1% BSA solution). A 1:1000 dilution of each of the serum samples collected from the immunized mice (50 µl) was added to $10^6$ T cell clones, mixed well and incubated for 30 minutes at 4° C. Following the incubation, the cells were washed 3x with 1% BSA solution, then incubated for 30 minutes in 50 µl of a detecting antibody (Goat anti-mouse immunoglobulin, Fluorescein isothiocyanate conjugated; Zymed Laboratories, San Francisco, Calif.) diluted 1:40 in 1% BSA solution. The cells were washed 3x in 1% BSA solution, then fixed with 1% paraformaldehyde solution (paraformaldehyde dissolved in Dulbecco's phosphate buffered saline; Sigma Chemical Co., St. Louis, Mo.). The samples were then analyzed on a FACSort™ flow cytometer (Bectin-Dickinson, San Jose, Calif.). The mouse sera exhibiting the highest degree of fluorescence on the T cell clones was selected for cell fusion to create the monoclonal antibodies.

3. Preparation of Hybridomas

After the mouse with the best antibody titre to the T cell clones was selected, it was rested for a total of 4 weeks after its last immunization. It was then boosted with $10^7$ T cell clones by intraperitoneal injection in Dulbecco's phosphate buffered saline. Four days later, the mouse was euthanized by cervical dislocation and the spleen was removed and teased apart into a cell suspension and washed in Dulbecco's phosphate buffered saline. The spleen cells were then counted and mixed with SP 2/0 myeloma cells (ATCC Accession No. CRL8006, Rockville, Md.) that are incapable of secreting either heavy or light immunoglobulin chains (Kearney et al., Journal of Immunology, 1979, 123:1548) at a ratio of 2:1 (Spleen cell:myeloma cells) and then fused using polyethylene glycol 1450 (ATCC, Rockville, Md.) according to the standard procedure developed by Kohler and Milstein (*Nature,* 1975, 256:495) in eight 96-well tissue culture plates in selective HAT medium.

Between 10 and 21 days after fusion, hybridoma colonies become visible and were screened by flow cytometry using T cell clones, as described above. All hybridoma colonies that gave a positive response with the T cell clones were expanded to 24-well cultures and subcloned by limiting dilution to produce monoclonal cell lines. At this point, additional screening was done with the hybridomas to identify which hybridoma produces an anti-CTLA-4 antibody. Culture media harvested from hybridoma cultures (supernatants) were screened by ELISA (enzyme-linked immuno-adsorbent assay) with a panel of known T cell surface antigens including CTLA-4. The ELISA was performed by coating high protein binding 96-well EIA plates (Costar, Cambridge, Mass.) with 50 µl/well of a 1 µg/ml solution (0.02 µg/well) of human CTLA-4-Ig, which has the extracellular binding portion of CTLA-4 coupled to an Fc portion of an immunoglobulin (Repligen Corporation, Cambridge, Mass.) dissolved in Dulbecco's phosphate buffered saline, pH 7.2, (PBS) overnight at 4° C. The CTLA-4-Ig was aspirated off the plates and the plates were thoroughly washed with PBS (3x). The plates were then blocked with 1% BSA solution for 1 hour at room temperature to inhibit non-specific binding. After the plates were sufficiently blocked, the BSA solution was removed and 50 µl/well of hybridoma supernatant was added. The plates were incubated for 45 minutes at 37° C., then washed 3× with PBS. A detecting antibody (Goat anti-mouse Ig, Horse Radish Peroxidase conjugated; Zymed Laboratories, San Francisco, Calif.) was then diluted 1:4000 in PBS and 50 μl was added to each well for 45 minutes at 37° C. The plates were then washed again with PBS, followed by the addition of 50 μl/well of 1 mM ABTS in a 0.1 M Sodium citrate solution, pH 4.2 (2,2-azino-bis-3-ethylbenzthiazoline-6-sulfonic acid; Zymed Laboratories, San Francisco, Calif.) to which a 1:1000 dilution of 30% Hydrogen peroxide had been added for 30 minutes at room temperature in the dark. The samples having hybridoma supernatants containing antibodies to human CTLA-4 were indicated as a green color which forms as the peroxidase reacts with the ABTS and hydrogen peroxide. The intensity of the green color (absorbance at 405 nm) was assessed on a Bio-Rad microplate reader (Bio-Rad Laboratories, Hercules, Calif.). Two mouse anti-human CTLA-4 monoclonal antibodies, A3.4H2 and A3.6B10, were identified.

Example 2

Analysis of Anti-CTLA-4 Monoclonal Antibodies

The monoclonal antibodies were examined to determine the subclass of the antibody using an ISOstrip Kit (Boehringer Mannheim, Indianapolis, Ind.). 5 μl of hybridoma supernatant was diluted in PBS and added to a test tube containing blue latex beads bound to anti-mouse Ig antibodies. An isotyping strip was then placed in each tube and the bead/antibody solution moves up the strip by capillary action until the solution passed an antibody bound line containing antibodies specific for the different isotypes. A blue line appeared in the area of the strip for each isotype detected in the hybridoma supernatant. Both A3.4H2 and A3.6B10 were found to be of the IgG2a subclass with kappa light chains.

Subclones of the hybridomas were analyzed by ELISA and flow cytometry using a CTLA-4-transfected CHO cell line (obtained from Dr. Gordon Freeman through the Repligen Corporation, Cambridge, Mass.). The antibodies were also tested for their ability to block B7.1 and B7.2, the natural ligands for the CTLA-4 receptor, from binding to CTLA-4. Both A3.4H2 and A3.6B10 were able to block B7 ligand binding (Table 1).

TABLE 1

| | A3 Fusion ELISA | | |
|---|---|---|---|
| Hybridoma | Isotype | Negative Control | CTLA4-Ig |
| A3.4H2 | IgG2a,k | 0.175 | 1.381 |
| A3.6B10 | IgG2a,k | 0.000 | 1.215 |

Example 3

Separation and Sequencing of the Heavy and Light Chains of Anti-CTLA-4 Monoclonal Antibody The antibody may be isolated from the hybridomas and purified by any method known in the art. At least two methods may be used to separate the heavy and light chains of the purified antibody for sequence determination. The first method employs a semi-preparative SDS-PAGE followed by electroblotting onto a polyvinyldifluoride (PVDF) membrane. Briefly, the purified antibody is subjected to slab gel electrophoresis in SDS after reduction with 2-merecaptoethanol. The resolved heavy and light chains are then transferred onto a membrane such as an IMMOBILON® membrane (a PVDF membrane from Millipore, Bedford, Mass.) using the electroblotting method of Matsudaira [J. Biol. Chem. 261:10035 (1987)]. Bands corresponding to the heavy and light chains which are identified with Coomassie Brilliant Blue staining may then be excised from the membrane and processed for N-terminal sequencing.

A second more complicated method permits larger amounts of the heavy and light chains to be isolated in solution. This method involves a dialysis step in which the purified antibody sample is dialyzed against 0.1M Tris-HCl, 1 mM EDTA, pH 8.0, at 4° C. and then subjected to oxidative sulfitolysis in $NaSO_3Na_2S_2O_0$, essentially as described by Morehead at al. [Biochemistry 23:2500 (1984)]. Following sulfitolysis, the antibody preparation is dialyzed against 1M acetic acid lyophilized to dryness, reconstituted in 1M acetic acid, and subjected to gel filtration in a 1×30 cm SEPHADEX G-75® column in 1M acetic acid. The purity of the heavy and light chains following this step can then be assessed by analytical SDS-PAGE and then concentrated for sequencing.

N-terminal amino acid sequencing may be performed using any commercial amino acid sequencer such as an Applied Biosystems Model 477A protein-peptide sequencer. Analysis of the isolated chains is performed following the instructions of the manufacturer of the sequencer.

Example 4

Oligonucleotide Primer Design and Cloning of Anti-CTLA-4 Monoclonal Antibody

1. Preparation of Oligonucleotides

Based upon the information which is obtained from the foregoing amino acid sequence analyses, degenerate oligonucleotide primers can be designed for use in PCR. Other non-degenerate primers may be designed based upon nucleotide sequence information obtained following PCR amplification of cDNA encoding the complete heavy and light chains (described below).

Oligonucleotide primers are synthesized by standard methods using a commercially available sequencer such as an Applied Biosystems Model 380B Synthesizer.

Alternatively PCR amplification of the $IgG_1$ Fd heavy chain fragments and light chains may be performed using the individual heavy and light chain variable region gene families, and 3' constant region primers for $IgG_1$, k or 1 as previously described (Kang et al., in "Methods, A Companion to Methods in Enzymology: Vol. 2", R. A. Lerner and D. R. Burton, ed. Academic Press, NY, pp 111–118,1991). Such primers can be commercially obtained from commercial sources such as Operon (Alameda, Calif.). Primers may contain restriction enzyme sites to allow the sequential ligation of Fd and light chain libraries for various other recombinant uses into a phage display vector.

2. PCR Amplification of Heavy and Light Chains

Total cytoplasmic RNA can be isolated from the hybridoma cell lines by any method known in the art such as by lysing the cells in a lysis buffer consisting of 10 mM Tris-HCl, pH 7.4, 10 mM NaCl, 2 mM $MgCl_2$ and 0.5% Nonidot P40 followed by centrifugation to separate nuclear and cytoplasmic fractions. The nuclear pellet is discarded and the supernatant fluid is mixed with an equal volume of a solution containing 200 mM NaCl, 10 mM Tris-HCl, pH 7.4, 20 mM elbylenediamineteiraacetate (EDTA) and 2% sodium dodecylsulfate (SDS). The mixture is extracted once with an equal volume of Tris-buffered phenol/chloroform (1:1) and once with chloroform. Following the extractions, the mixture is precipitated with sodium acetate and absolute ethanol at −20° C. The method may be performed by commercially available kits such as that sold by Stratagene, La Jolla, Calif.

The first strand cDNA may be synthesized directly from total cytoplasmic RNA at 37° C. for 90 minutes using reverse transcriptase in a reaction buffer, such as that sold by Gibco-BRL, Grand Island, N.Y.

Polymerase chain reaction (PCR) amplifications may then be carried out using a Techne programmable thermal cycler or similar equipment. The PCR reaction mixture generally consists of 10 μl of first strand cDNA reaction mixture, 53.5 ml of distilled H20, 10 μl of 10× Taq polymerase reaction buffer (500 mM KCL. 100 mM Tris-HCl, pH 8.3, 15 mM $MgCl_2$, 0.1% gelatin), 16 μl of 1.25 mM dNTP mixture (DATP, TTP, dCTP, dGTP), 5 μl of each primer of interest (20 pmol/μl) and 0.5 μl of DNA polymerase.

After PCR the DNA mixtures are subjected to electrophoresis in agarose gels containing ethidium bromide. The PCR fragments of interest may then be excised from the gels and purified by electroelution.

3. Subcloning and DNA Sequencing

The gel-purified PCR fragments are digested with restriction enzymes such as Not I and SpeI and then ligated to an appropriate vector such as dephosphorylated Not I/SpeI digested Bluescript plasmid vector. Competent cells such as *E. coli* strain DH5-alpha (Max Efficiency) cells are transformed with the ligation mixture or introduced into a phagemid library for subsequent recombination procedures.

Double stranded plasmid DNA is purified by any technique known in the art for purifying DNA, such as the Qiagen plasmid maxiprep kit (Qiagen, Chatsworth, Calif.). Sequencing is then performed on an automated DNA sequencer (e.g., Applied Biosystems, Inc. (ABI), Foster City, Calif.), using a Taq fluorescent dideoxy terminator cycle sequencing kit (ABI). Derived sequences for heavy chain Fd fragments and light chains can then be aligned using MacVector and the Genbank database (International Biotechnologies Inc., New Haven, Conn.).

Deposits

Hybridoma A3.4H2 and A3.6B10 were deposited on Mar. 21, 1997, with the American Type Culture Collection (ATCC), 10801 University Boulavard, Manassas, Va. 20220-2209, as ATCC Accession No. HB-12319 and HB-12318.

Applicants' assignee, the Brigham and Women's Hospital, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. 122. The deposited material will be maintained with all the care necessary to keep it viable and uncontaminated for a period of at least five years after the most recent request for the furnishing of a sample of the deposited hybridoma, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

The foregoing written specification is to be considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of the invention. Similarly, the particular antibodies and peptides disclosed herein are not to be construed as limiting of the invention as they are intended merely as illustrative of particular embodiments of the invention as enabled herein. Therefore, any cell lines, antibodies, and peptides that are functionally equivalent of those described herein are within the spirit and scope of the claims appended hereto. Indeed, various modifications of the invention in addition to those shown and described herein will become apparent to those skilled in the art from the foregoing description and fall within the scope of the appended claims.

All references, patents and patent publications that are recited in this application are incorporated in their entirety herein by reference.

We claim:

1. A composition, comprising an isolated CTLA-4 specific antibody or antibody fragment that selectively binds to human CTLA4 and co-stimulates T-cell proliferation, wherein the isolated CTLA-4 specific antibody or antibody fragment comprises a CDR selected from the group consisting of a CDR from monoclonal antibody$_{A3.4H2}$ produced by hybridoma A3.4H2 deposited under ATCC Accession No. HB-12319 and a CDR from monoclonal antibody$_{A3.6B10}$ produced by hybridoma A3.6B10 deposited under ATCC Accession No. HB-12318.

2. The composition of claim 1, wherein the isolated CTLA-4 specific antibody or antibody fragment comprises a CTLA-4 binding CDR3 region.

3. The composition of claim 2, wherein the CTLA-4 binding CDR3 region is a CDR3$_{A3.4H2}$ of a monoclonial antibody produced by hybridoma A3.4H2 deposited under ATCC Accession No. HB-12319.

4. The composition of claim 2, wherein the CTLA-4 binding CDR3 region is a CDR3$_{A3.6B10}$ of a monoclonal antibody produced by hybridoma A3.6B10 deposited under ATCC Accession No. HB-12318.

5. The composition of claim 1, wherein the isolated CTLA-4 specific antibody or antibody fragment is an intact soluble monoclonal antibody.

6. A composition, comprising monoclonal antibody$_{A3.4H2}$ produced by a hybridoma cell line deposited under ATCC Accession No. HB-12319.

7. A composition, comprising monoclonal antibody$_{A3.6B10}$ produced by a hybridoma cell line deposited under ATCC Accession No. HB-12318.

8. The composition of claim 1, wherein the isolated CTLA-4 specific antibody or antibody fragment is a humanized monoclonal antibody.

9. The composition of claim 1, wherein the isolated CTLA-4 specific antibody or antibody fragment is a monoclonal antibody fragment selected from the group consisting of an F(ab')$_2$ fragment, an Fd fragment, and an Fab fragment.

10. The composition of claim 1, wherein the isolated CTLA-4 specific antibody or antibody fragment comprises a light chain CDR2 region selected from the group consisting of a CDR2$_{A3.4H2}$ of a monoclonal antibody produced by hybridoma A3.4H2 deposited under ATCC Accession No. HB-12319 and a CDR2$_{A3.6B10}$ of a monoclonal antibody produced by hybridoma A3.6B10 deposited under ATCC Accession No. HB-12318.

11. The composition of claim 1, wherein the isolated CTLA-4 specific antibody or antibody fragment comprises a light chain CDR1 region selected from the group consisting of a $CDR1_{A3.4B2}$ of a monoclonal antibody produced by hybridoma A3.4H2 deposited under ATCC Accession No. HB-12319 and a $CDR1_{A3.6B10}$ of a monoclonal antibody produced by hybridoma A3.6B10 deposited under ATCC Accession No. HB-12318.

12. A hybridoma cell line deposited under ATCC Accession No. HB-12319.

13. A hybridoma cell line deposited under ATCC Accession No. HB-12318.

14. A composition, comprising:
an effective amount for promoting T cell proliferation of an isolated CTLA-4 specific antibody or antibody fragment that selectively binds to human CTLA-4 and co-stimulates T-cell proliferation; and,
a pharmaceutically acceptable carrier,
wherein the isolated CTLA4 specific antibody or antibody fragment comprises a CDR selected from the group consisting of a CDR from monoclonal antibody$_{A3.4H2}$ produced by hybridoma A3.4H2 deposited under ATCC Accession No. HB-12319 and a CDR from monoclonal antibody$_{A3.6B10}$ produced by hybridoma A3.6B10 deposited under ATCC Accession No. HB-12318.

15. The composition of claim 14, wherein the isolated CTLA-4 specific antibody or antibody fragment comprises a CTLA-4 binding CDR3 region.

16. The composition of claim 15, wherein the CTLA-4 binding CDR3 region is a $CDR3_{A3.4DH2}$ of a monoclonal antibody produced by hybridoma A3.4H2 deposited under ATCC Accession No. HB-12319.

17. The composition of claim 15, wherein the CTLA-4 binding CDR3 region is a $CDR3_{A3.6B10}$ of a monoclonal antibody produced by hybridoma A3.6B10 deposited under ATCC Accession No. HB-12318.

18. The composition of claim 14, wherein the isolated CTLA-4 specific antibody or antibody fragment is selected from the group consisting of a soluble intact monoclonal antibody and a functionally active monoclonal antibody fragment.

19. The composition of claim 14, wherein the isolated CTLA-4 specific antibody or antibody fragment is a humanized antibody.

20. The composition of claim 14, wherein the isolated CTLA-4 specific antibody or antibody fragment is monoclonal antibody$_{A3.4H2}$ produced by a hybridoma cell line deposited under ATCC Accession No. HB-12319.

21. The composition of claim 14, wherein the isolated CTLA-4 specific antibody or antibody fragment is monoclonal antibody$_{A3.6B10}$ produced by a hybridoma cell line deposited under ATCC Accession No. HB-12318.

22. The composition of claim 14, wherein the isolated CTLA-4 specific antibody or antibody fragment is a monoclonal antibody fragment selected from the group consisting fan $F(ab')_2$ fragment, an Fd fragment, and an Fab fragment.

23. The composition of claim 14, wherein the isolated CTLA-4 specific antibody or antibody fragment comprises a light chain CDR2 region selected from the group consisting of a $CDR2_{A3.4H2}$ of a monoclonal antibody produced by hybridoma A3.4H2 deposited under ATCC Accession No. HB-12319 and a $CDR2_{A3.6B10}$ of a monoclonal antibody produced by hybridoma A3.6B10 deposited under ATCC Accession No. HB-12318.

24. The composition of claim 14, wherein the isolated CTLA-4 specific antibody or antibody fragment comprises a light chain CDR1 region selected from the group consisting of a $CDR1_{A3.4H2}$ of a monoclonal antibody produced by hybridoma A3.4H2 deposited under ATCC Accession No. HB-12319 and a $CDR1_{A3.6B10}$ of a monoclonal antibody produced by hybridoma A3.6B10 deposited under ATCC Accession No. HB-12318.

* * * * *